United States Patent [19]

Walter

[11] 4,188,493
[45] Feb. 12, 1980

[54] PROCESS FOR RECOVERING CMOS

[75] Inventor: Thomas J. Walter, Baton Rouge, La.

[73] Assignee: Ethyl Corporation, Richmond, Va.

[21] Appl. No.: 781,574

[22] Filed: Mar. 28, 1977

[51] Int. Cl.$^2$ .................. C07C 59/23; C07C 51/42
[52] U.S. Cl. .................................................. 562/580
[58] Field of Search .................. 260/535 P; 562/583, 562/580

[56] References Cited

U.S. PATENT DOCUMENTS 4,014,929   3/1977   Stahlheber .................. 260/535 P

*Primary Examiner*—Paul J. Killos
*Attorney, Agent, or Firm*—Donald L. Johnson; John F. Sieberth; Paul H. Leonard

[57] ABSTRACT

It is disclosed that water soluble salts of carboxyalkyloxy succinic acids can be obtained in a form containing less than usual contamination by alkaline earth metal and related substances by treating the contaminated salts with alkali metal carbonate and separating (e.g., filtering) at an elevated temperature and at a selected pH region. The most important factor in obtaining this improvement is the use of the proper separating temperature, preferably within the range of 70°–125° C., especially a temperature of about 100° C. In addition, the use of certain conditions of pH minimizes side reactions.

16 Claims, No Drawings

PROCESS FOR RECOVERING CMOS

BACKGROUND OF THE INVENTION

1. Field of the Invention

This invention relates in general to the preparation of water soluble salts of carboxyalkyloxy succinic acids and in particular to the preparation of a highly pure form of said salts having low contamination with alkaline earth metals and related sequesterable substances.

2. Description of the Art

It is known that water soluble salts of carboxyalkyloxy succinic acids are useful detergent builder materials. Such is disclosed in U.S. Pat. No. 3,635,830. The preparation of such materials is described in U.S. Pat. No. 3,914,297; however, the preparation of the materials in a form as low in alkaline earth metals and related substances as is desirable is difficult. Especially is it evident that not only does the prior art fail to teach in regard to minimizing contamination by alkaline earth metals and related substances but the prior art does not even recognize the residual contamination problem.

It is known that the typical water soluble carboxymethyloxy succinic acid (CMOS) salts are readily produced by reacting salts of glycolic acid and maleic acid in an aqueous medium in the presence of enough zinc or alkaline earth metal hydroxide, typically calcium hydroxide, to produce a salt system having a pH of at least about 8 and preferably higher than about 11, e.g. 12.1, when measured at 25° C. The reaction is preferably conducted at reflux temperature at about atmospheric pressure for from about 1 to about 6 hours. Typically, the calcium salt system thus obtained is reacted with an alkali metal carbonate such as sodium or potassium carbonate at a moderate temperature of about 60° C., for example, and filtered directly or after cooling to room temperature of about 25° to 30° C. to remove suspended zinc or alkaline earth metal carbonate yielding an aqueous solution containing trisodium CMOS salts or tripotassium CMOS salts as appropriate. Such solutions can also be produced in other ways such as by converting the zinc or alkaline earth metal salt into acid by ion exchange treatment with mineral acid and reacting the CMOS with an organic or inorganic base to produce other salts typified herein such as the ammonium or alkanol ammonium salts.

SUMMARY OF THE INVENTION

Since the use of alkali metal salts of carboxyalkyloxy succinic acids as detergent builders involves an ability of such salts to sequester Group IIA ions such as magnesium, calcium, strontium, barium, and other sequesterable ions in an aqueous system, it is desired to produce a product having the maximum sequestration ability which makes it desirable to remove all residual alkaline earth metal or zinc from the salts in the production process; however, the process of producing the salts introduces the ions and the sequestration property itself makes complete removal of sequesterable ions virtually impossible.

Various approaches have been tried to remove or reduce residual alkaline earth metal, zinc and other sequesterable ions contained in the water soluble salts of carboxyalkyloxy succinic acid; however, it has been difficult to find a simple low cost process. Treatment of the alkaline earth metal or zinc salt with an acid such as sulfuric acid can produce (1) a calcium salt of the treating acid and (2) CMOS following which the latter is separated and converted to an alkali metal salt, for example, by subsequent treatment with a base such as an alkali metal hydroxide; however, this is expensive due to the plural steps, the stoichiometric amounts of treating acid and hydroxide reagents required and because the calcium values are lost to the process and cannot be recycled.

The present invention alleviates the foregoing problems to a significant extent making it possible to reduce the alkaline earth metal or zinc contamination of water soluble carboxyalkyloxy succinic acid salts obtained via a carbonate exchange operation. As a result, it is possible to produce typical aqueous solutions of trisodium CMOS salt having ≦100 parts per million of calcium from which a solid tetrahydrate trisodium salt can be obtained having ≦500 parts per million of calcium. These relatively low amounts of calcium are about half that usually contained in the respective products from a carbonate exchange process prior to the advent of the present process. In addition, a significant proportion of the calcium values can be recovered and recycled in the process.

In the present process, advantage is taken of the newly discovered effect of temperature upon equilibria in the carbonate exchange reaction of alkali metal carbonate and alkaline earth metal or zinc salts of carboxyalkyloxy succinic acid and especially in the separation of the alkaline earth metal or zinc carbonate precipitate produced by the exchange reaction.

It has been discovered that a more complete separation of the alkaline earth metal or zinc ions from the solution containing the water-soluble CMOS salt is obtained when the separation is conducted at a higher temperature than the 60° C. maximum of the prior art. Separation temperatures of 70° C. and higher are preferred; however, since undesired side reactions occur at increasing rates as temperature is increased, it is preferred to avoid prolonged contacting especially at temperatures in excess of about 125° C.

In general, the separation preferably is preceded by a brief contact period ranging from several seconds to several hours at a temperature of from about 70° to about 125° C. This "cook" period wherein the carbonate exchange is usually performed with a slight excess of alkali metal carbonate or other suitable carbonate, when performed at the present temperatures rather than at 60° C. or lower, enhances the attainment of equilibrium conditions in the carbonate exchange which favor the more complete removal of alkaline earth metal or zinc ions. A more preferred temperature range for the contacting as well as the separation is from about 85° to about 100° C., especially about 100° C., where the principal benefits of the invention are realized without incurring the problems attendant to operation at super atmospheric pressure. Useful contacting times range from about 5 seconds to about 5 hours, preferably from about 10 to about 60 minutes, preferably about 30 minutes.

In addition to the discovery of the importance of temperature in the separation operation, it has been discovered that the pH of the system at the separation step and during the preceding "cook" period for the exchange reaction or for an equilibrium establishment is also an important consideration because of a beneficial effect of pH in suppressing undesired side reactions at the elevated separation temperatures of the present process. Thus where the prior art made no attempt to adjust either temperature or pH at the exchange reaction or at separation for the purposes of achieving a more complete removal of alkaline earth metal or zinc ions in the separation step or of avoiding side reactions, the process of the present invention preferably controls both temperature and pH.

Preferred pH of the calcium CMOS or carboxyalkyloxy succinic acid solution prior to combination with sodium carbonate is from about 5 to about 10, preferably from about 6 to about 9, typically about 7.

When using a typical pH of 7, the formation of by-product fumaric acid salts during the exchange or equilibrating reactions as well as during the separation is controlled being held to a reasonably low value.

As shown in greater detail in the examples that follow, the calcium content in tetrahydrate trisodium carboxymethyloxy succinic acid salts can be reduced from about 1000 parts per million which is typical for the product obtained when the separation is conducted at about room temperature to less than 500 parts per million when separation is performed at 100° C. The adjustment of pH from a typical prior art reaction value of 12.1 to the region of 7 by the addition of a small amount of sulfuric or other suitable acid limits product losses due to the formation of fumaric acid salts even when using a "cook" period for the carbonate exchange reaction at 100° C. prior to the 100° C. filtration. Without the pH adjustment, the fumaric acid salt level attained after a 15 minute "cook" at 100° C. and filtration at 100° C. is 5 percent or higher. Although the fumaric acid salt can be separated from the alkali metal CMOS salt, the conversion to fumarate represents a loss of alkali metal CMOS salt value and hence is desirably avoided to provide a minimum cost product.

DISCUSSION

Generally, salts produced by the present invention which are useful as builders and which can be improved in accordance with the present process are water soluble particulate hydrate salts of acids of the formula:

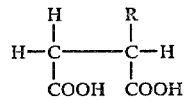

wherein R is a carboxyalkyloxy radical (—OR'COOH) having from 2 to about 7 carbon atoms total, R' preferably being a "divalent, straight chain alkyl" structure [—(CH$_2$)$_n$—] where n is 1–6. Examples of such acids are carboxymethyloxy succinic acid, carboxybutyloxy succinic acid, carboxyhexyloxy succinic acid, carboxyisobutyloxy succinic acid, and the like. A preferred acid has been found to be carboxymethyloxy succinic acid because alkali metal and other water soluble salts thereof are readily produced at low cost and are effective and useful detergent builders.

Typical useful water soluble salts of carboxymethyloxy succinic acid are alkali metal, ammonium and lower alkanol ammonium salts having from 2 to about 6 carbon atoms in the alkanol structure such as sodium salts, potassium salts, ammonium salts, triethanol ammonium salts, diethanol ammonium salts, monoethanol ammonium salts, monoisopropanol ammonium salts, mono-n-butanol ammonium salts, and the like and mixtures of two or more of such.

Preferred salts are the sodium, potassium and ammonium salts, with sodium salts being particularly preferred because of low cost, effectiveness and ease of production.

The builders of this invention can be used to advantage with a wide variety of detergent actives or surfactants, including those known in the art as anionic, cationic, nonionic, ampholytic and zwitterionic detergents as well as any suitable mixture of such detergents. Included also are various soaps such as those of natural or synthetic origin or derivation, having "coconut" or "tallow" molecular weight range, as well as soaps of straight chain or branched chain carbon skeleton structures.

Typical detergent mixtures contain the builders of this invention with or without one or more other builders such as salts of other polycarboxylic acids, typically oxydisuccinic acid, nitrilotriacetic acid, phosphoric acid, tartaric acid, tetrahydrofuran tetracarboxylic acid, and citric acid; plus one or more of the conventional actives or adjuvants such as alkyl benzene sulfonates, olefin sulfonates, sulphobetaines, alcohol sulfates, alcohol alkoxy sulfates, amides, amine oxides and the like. When the resultant washing compositions are used in aqueous washing systems, the cleaning power of the formulation is enhanced in much the same way as when the commonly used alkali metal polyphosphate salt builders are employed as the only builders, yet the present builder systems do not contribute to or magnify the eutrophication problems characteristic of phosphorus-containing builders. The builders of the present invention are generally used in formulations containing other agents such as abrasives, dyes, perfumes, anti-redeposition agents, pH modifers, inorganic salts such as sodium chloride, lime-soap dispersants, brighteners, bacteriostats, water hardness additives and the like.

From the results obtained with the present process, it is believed that a complex equilibrium exists as represented by the following equations and that the overall equilibrium is shifted toward the right at higher temperatures.

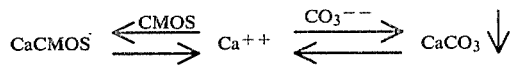

Raising the temperature, e.g. from 30° to 100° C., apparently thus favors the precipitation of CaCO$_3$ from the system which enhances the removal of the undesired calcium or other Group IIA or other sequesterable ions as the carbonate provided the separation is performed at the elevated temperature. Merely heating the total mixture and then allowing it to cool prior to separation apparently permits the equilibrium to shift toward the left before the separation occurs so that the benefits of the present invention are not realized. Separation then performed can be by any suitable procedure such as filtration, centrifuging, decanting, settling and the like.

The formation of fumaric acid salts is believed to proceed according to a different mechanism and to be enhanced by strongly alkaline conditions brought about by the reaction of excess lime (left over from the first reaction of maleic acid and glycolic acid) with sodium carbonate according to the reaction:

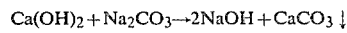

When the pH of the system is adjusted as described herein, not only is the elimination of calcium facilitated but the by-product NaOH is converted to salt of the neutralizing acid. Preferred acid used for pH adjustment is an organic acid or a strong mineral acid such as $H_2SO_4$, HCl, $HNO_3$, $H_2CO_3$, $H_3PO_4$, acetic acid, maleic acid, glycolic acid and CMOS. In general, only a small amount of acid is required. In some instances, it is convenient to generate the $H_2CO_3$ in situ by feeding $CO_2$.

Preferred acids are $H_2SO_4$ and acetic acid, only a small amount of such being required. Acetic acid has an advantage in that resultant sodium acetate is readily separated. The other organic acids exemplified are either reactants or contain the CMOS ion and hence have the advantage that they do not represent foreign materials.

Other typical salts that may be processed in accordance with the teachings of the present invention include: sodium carboxyethyloxy succinate, potassium carboxyethyloxy succinate, ammonium carboxyethyloxy succinate, monoethanol ammonium carboxyethyloxy succinate, diethanol ammonium carboxyethyloxy succinate, triethanol ammonium carboxyethyloxy succinate, sodium carboxypropyloxy succinate, sodium carboxybutyloxy succinate, sodium carboxyamyloxy succinate, sodium carboxyhexyloxy succinate.

The foregoing salts exist in various hydrated forms with various amounts of water of hydration in the hydrated salt.

Accordingly, the present invention is directed to an improvement in a process for recovering water soluble salts of carboxyalkyloxy succinic acids from an aqueous system thereof containing a precipitate of alkaline earth metal or zinc carbonate, the improvement residing in separating the precipitate from the system at a temperature of from about 70° to about 125° C. Preferably the separation temperature is from about 85° to about 100° C., especially about 100° C.

Preferably, the separation is preceded by a contacting period of from about 5 seconds to about 5 hours at a temperature of from about 85° to about 100° C., especially a period of from about 10 to about 60 minutes, typically about 30 minutes.

Preferably, the system is produced by combining an aqueous solution of alkaline earth metal or zinc carboxyalkyloxy succinic acid salt with an alkali metal carbonate. Preferred water soluble salt of carboxyalkyloxy succinic acid is an alkali metal salt, especially sodium or potassium salt. Preferably, the salt is a salt of carboxymethyloxy succinic acid. Preferably the salt is a trisodium or tripotassium carboxymethyloxy succinic acid salt. Preferably, the pH of such alkaline earth metal or zinc carboxyalkyloxy succinic acid salt solution prior to combining with alkali metal carbonate is from about 5 to about 10, especially from about 6 to about 9, typically about 7.

Preferably, the desired pH is obtained by acidifying a more basic solution of alkaline earth metal or zinc carboxyalkyloxy succinic salt with a suitable organic acid or mineral acid. Preferably the acidifying acid is a mineral acid, such as sulfuric acid. Alternately a suitable acidifying acid is acetic acid.

Preferably, the separating is accomplished by centrifuging.

EXAMPLES 19.6 grams of maleic anhydride, 100 ml of water, 23.7 grams of 70 percent technical glycolic acid and enough lime to raise the pH to 12.1 as measured at about 25° C. by pH paper (manufactured by E. Merck, Darmstadt, Germany) were combined and then heated to 100° C. and held at that temperature with stirring for 2–3 hours until conversion reached at least 90 percent as measured by NMR. The amount of lime used is about 105 percent of the stoichiometric amount required for complete reaction based on the maleic anhydride fed. This reaction produces the calcium salt of CMOS.

For convenience, the solution was cooled to room temperature. Subsequently approximately 0.85 gram of $H_2SO_4$ was added to the calcium salt CMOS system to provide a system pH of 7.0. The system was then added to a mixture of 40 grams $Na_2CO_3$ and 25 ml of water at 60° C. over a period of 45 minutes. The resulting mixture was heated to 100° C. over a 30 minute period and held at that temperature for 30 minutes then filtered while still at 100° C. The amount of sodium carbonate used represents a 3 percent excess over the stoichiometric amount required for reaction of the lime added initially. The filtrate was analyzed for calcium by atomic absorption and for organics by NMR after normalization to about 25 wt. percent NaCMOS salt content. Data are tabulated for this and other examples showing the content of calcium and the distribution of the organic constituents.

In Example 2, acetic acid was used for pH adjustment. Examples 3 and 4 were conducted with $H_2SO_4$ and acetic acid adjustment respectively, with the calcium salt of CMOS being added to the sodium carbonate at 85° C. rather than 60° C., followed by a 60 minute contacting period at 85° C. and filtration at 85° C. The increased calcium in the 85° C. filtrate is evident.

The addition, contacting and filtration procedure of Example 1 was used with Examples 2 and 5. The addition, contacting and filtration procedure of Examples 3 and 4 was used with Example 6.

Examples 5, 6 and 7 did not use pH adjustment. Example 5 shows the value of pH control in comparison to Examples 1 and 2.

Examples 7 and 8 are comparative in regard to calcium content resulting from performing the contacting and the separation at a temperature of 60° and show the higher calcium content obtained at such temperature. In these examples, the calcium salt of CMOS was added to sodium carbonate at 60° C., contacted for 1 hour at 60° C., then filtered at 60° C.

Example 9 was performed for comparative purposes to show the effect on calcium content of performing the contacting at 60° C. for one hour then cooling to 25° C., stirring for ½ hour at 25° C. and separation by filtration at 25° C. The calcium content was 533 ppm.

Table I

| Example | Filtration Temperature (°C.) | pH Adjustment | | Calcium in Filtrate (ppm) | Normalized Mol % Organics | | |
|---|---|---|---|---|---|---|---|
| | | pH | Acid | Amount (grams) | | CMOS | Maleate | Fumarate |
| 1 | 100 | 7 | $H_2SO_4$ | 0.85 | 90 | 93.5 | 3.6 | 2.9 |

Table I-continued

| Example | Filtration Temperature (°C.) | pH Adjustment | | | Calcium in Filtrate (ppm) | Normalized Mol % Organics | | |
|---|---|---|---|---|---|---|---|---|
| | | pH | Acid | Amount (grams) | | CMOS | Maleate | Fumarate |
| 2 | 100 | 7 | Acetic Acid | 1.0 | 93 | 92.7 | 4.6 | 2.7 |
| 3 | 85 | 5.5 | $H_2SO_4$ | 1.25 | 126 | 94.6 | 3.4 | 2.0 |
| 4 | 85 | 7 | Acetic Acid | 1.17 | 160 | 92.2 | 4.2 | 3.6 |
| 5 | 100 | None | — | — | 96 | 90.2 | 4.0 | 5.7 |
| 6 | 85 | None | — | — | 111 | 90.6 | 4.2 | 5.3 |
| 7 | 60 | None | — | — | 220 | 95.4 | 2.9 | 1.8 |
| 8 | 60 | 7 | $H_2SO_4$ | 1.0 | 220 | 93.9 | 4.1 | 2.0 |
| 9 | 25 | None | — | — | 533 | 92.4 | 5.2 | 2.4 |

I claim:

1. In a process for recovering water soluble salts of carboxyalkyloxy succinic acids from an aqueous system thereof containing a precipitate of alkaline earth metal or zinc carbonate, the improvement of adjusting the pH of the aqueous system to about 6 to 9, treating the pH-adjusted system with an alkali metal carbonate, maintaining the treated system at a temperature of from about 70° to about 125° C. and separating precipitated alkaline earth metal carbonate from the system while maintaining the temperature within said temperature range.

2. The process of claim 1 wherein the temperature is maintained from about 85° to about 100° C.

3. The process of claim 1 wherein the temperature is maintained about 100° C.

4. The process of claim 1 wherein the water soluble salt is an alkali metal salt.

5. The process of claim 1 wherein the water soluble salt is a sodium or potassium salt.

6. The process of claim 1 wherein the water soluble salt is a salt of carboxymethyloxy succinic acid.

7. The process of claim 1 wherein the water soluble salt of carboxyalkyloxy succinic acid is a trisodium or tripotassium carboxymethyloxy succinic acid salt.

8. The process of claim 1 wherein the pH of the aqueous system is adjusted to about 7.

9. The process of claim 1 wherein the desired pH is obtained by acidifying a more basic solution of said salt with a suitable organic acid or mineral acid.

10. The process of claim 9 wherein the acidifying acid is a mineral acid.

11. The process of claim 9 wherein the acidifying acid is sulfuric acid.

12. The process of claim 9 wherein the acidifying acid is acetic acid.

13. The process of claim 1 wherein the separating is accomplished by centrifuging.

14. The process of claim 1, wherein said water soluble salts of carboxyalkoxy succinic acids is the trisodium salt of carboxymethyloxy succinic acid obtained from the reaction of maleic acid and glycolic acid in an aqueous system in the presence of calcium hydroxide, the precipitate of alkaline earth metal or zinc carbonate is calcium carbonate, the alkali metal carbonate with which the system is treated is sodium carbonate, the precipitated alkaline earth metal carbonate separated is calcium carbonate, and said temperature is maintained within said ranges a period of time sufficient to reduce the calcium ion content of the filtrate to about 100 parts per million.

15. The process of claim 14, wherein the temperature is maintained from 85° to 100° C. and the period said temperature is maintained is from about 10 to 60 minutes.

16. The process of claim 15, wherein the pH of the aqueous system is adjusted to about 7.

* * * * *